(12) United States Patent
Himmelsbach et al.

(10) Patent No.: US 6,488,958 B1
(45) Date of Patent: Dec. 3, 2002

(54) PLASTERS CONTAINING ACTIVE SUBSTANCES

(75) Inventors: Peter Himmelsbach, Rübker Strasse; Helmut Linder, Graf-Anton-Weg; Katharina Broschk, Eppendorfer Weg; Marike Sinnen, Feldstrasse; Matthias Wasner, Rothenhauschaussee, all of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 08/982,358

(22) Filed: Dec. 2, 1997

(30) Foreign Application Priority Data

Dec. 5, 1996 (DE) .......................................... 196 50 471

(51) Int. Cl.⁷ ................................................ A61F 13/02
(52) U.S. Cl. ...................... 424/443; 424/444; 424/447; 424/448; 424/449; 604/304; 604/307; 602/41
(58) Field of Search ................................. 424/443, 444, 424/447, 448, 449; 604/304, 307; 602/41

(56) References Cited

U.S. PATENT DOCUMENTS

| 4,814,168 A | * | 3/1989 | Sablotsky et al. | ............. 424/78 |
| 5,306,503 A | | 4/1994 | Müller et al. | ................ 424/449 |
| 5,527,536 A | | 6/1996 | Merkle et al. | ............... 424/448 |

FOREIGN PATENT DOCUMENTS

| DE | 42 24 325 C1 | 2/1994 |
| EP | 0 305 756 A1 | 3/1989 |

* cited by examiner

Primary Examiner—Jose' G. Dees
Assistant Examiner—Michael A. Williamson
(74) Attorney, Agent, or Firm—Norris McLaughlin & Marcus

(57) ABSTRACT

Plasters containing active substance, comprising a backing material and, applied thereon, a hot-melt self-adhesive composition, characterized in that the hot-melt self-adhesive composition comprises at least one hyper-aemic active substance.

4 Claims, No Drawings

PLASTERS CONTAINING ACTIVE SUBSTANCES

The invention relates to plasters containing active substances, comprising a backing material and, applied thereon, a hot-melt self-adhesive composition which comprises the active substance or, if appropriate, two or more active substances that are delivered to the skin.

Transdermal therapeutic systems (TTS) are forms of administration of medicaments which deliver one or more medicaments to the skin over a defined period at their site of use. A distinction is made here between systemic and local administration forms. With systemic administration forms, the active substance passes through the skin into the blood circulation by diffusion and can act within the body as a whole. Local administration forms, on the other hand, act only at the sites of application. The active substance remains in the skin or in the underlying layers.

Numerous embodiments of such plasters have already been described, some of which operate in accordance with the reservoir principle, where the active substance is delivered, for example, by way of a membrane, in some cases also with a matrix system or with a more complex multilayer structure.

It is also known that the adhesive composition of the plaster can be employed as the matrix containing active substance. In addition to self-adhesive compositions applied from solution, hot-melt self-adhesive compositions have also been proposed for this purpose, for example in EP-A 663 431, EP-A 452 034, EP-A 305 757, DE-A 43 10 012, DE-A 42 22 334 and DE-C 42 24 325.

The active substance listed in these cases, if at all, have been systemic ones.

Active substance plasters which promote the circulation belong to the group of local therapeutic systems. The use of such plasters is indicated for treating rheumatic complaints, sciatica, lumbago, stiff neck, shoulder/arm pain and muscular strains and sprains, muscular aching or muscle, joint and nerve pain in the region of the locomotor system.

Capsaicin, belladonna and nonivamide are known active substances in such local, circulation-promoting plasters. Because of their use on the motility apparatus they are in general required to adhere strongly. Usually, the plasters are coated over their full area with a resin-rubber adhesive composition which comprises the active substance.

However, plasters of this kind, which usually have to be applied over a relatively large area, exhibit in some cases distinct mechanical skin irritations after removal in the case of sensitive patients. In some cases there are allergic reactions. After a prolonged period of wear, their removal is to some extent painful.

A further disadvantage of the known thermally active plasters with an adhesive composition based on natural rubber which is applied in the form of a solution with organic solvents to the plaster backing is the comparatively low rate of release of the active substance.

The object of the invention, therefore, was to develop circulation-promoting (hyperaemic) and thus thermally active plasters which should feature good activity, i.e. a relatively high rate of release, and good skin compatibility at the same time as having good adhesion. In addition, they should be able to be prepared with little technical complexity and in an environmentally compatible manner.

This object is achieved by active substance-containing plasters according to claim 1.

It has been found that hot-melt self-adhesive compositions are also suitable for the release of substances having a hyperaemic action and just a local action.

These active substances are primarily the known substances of cayenne pepper and also the synthetic capsacinoid NVA (nonivamide), and also nicotinic acid derivatives, preferably benzyl nicotinate or propyl nicotinate.

The concentrations are from 0.01 to about 20% by weight, preferably from 0.1 to 10% by weight.

With particular preference, the hot-melt adhesive compositions are based on synthetic thermoplastic polymers, such as synthetic rubbers, especially block copolymers, polyacrylates, polyurethanes, polyesters, polyolefins, polyacrylamides or silicones.

For systems with particularly strong adhesion the adhesive composition is based preferably on block copolymers, especially A-B or A-B-A block copolymers or mixtures thereof. The hard phase A is ideally polystyrene or its derivatives and the soft phase B comprises ethylene, propylene, butylene, butadiene, isoprene or mixtures thereof, with particular preference being given to ethylene and butylene or mixtures thereof.

Polystyrene blocks can also, however, be present in the soft phase B, in amounts of up to 20% by weight. The overall proportion of styrene, however, should always be less than 35% by weight. Preference is given to proportions of styrene of between 5% and 30%, since a lower proportion of styrene makes the adhesive composition more conformable.

The tailored blending of diblock and triblock copolymers is particularly advantageous, with preference being given to a proportion of diblock copolymers of less than 80% by weight.

In an advantageous embodiment the hot-melt pressure-sensitive adhesive composition has the following composition:

from 10 to 90% by weight of block copolymers,
from 5 to 80% by weight of tackifiers, such as oils, waxes, resins or mixtures thereof, preferably mixtures of resin and oils,
less than 60% of plasticizers
less than 15% by weight of additives
less than 5% by weight of stabilizers.

In a particularly preferred embodiment of an adhesive composition of this kind which is additionally provided with the hyperaemic active substance, the adhesive composition is based on an A-B/A-B-A block copolymer of styrene, ethylene and butylene having a styrene content of less than 35% by weight, and contains 0.1–10% by weight of nonivamide, preferably about 0.2% by weight.

Tackifiers used are the hydrocarbon oils, hydrocarbon waxes and hydrocarbon resins. In this context the oils, such as paraffinic hydrocarbon oils, or waxes, such as paraffinic hydrocarbon waxes, have a favourable effect on bonding to the skin owing to their consistency. Plasticizers used are long-chain fatty acids and/or their esters. These additives serve to adjust the adhesion properties and the stability. The addition of mineral fillers in minor amounts is also possible.

The adhesive compositions are adjusted such that at a frequency of 0.1 rad/s they have a dynamic-complex glass transition temperature of less than +10° C., preferably from −3° to −30° C. and, with very particular preference, from −6° to −25° C.

The tailored reduction in the glass transition temperature of the self-adhesive composition as a consequence of the selection of the tackifiers, the plasticizers and the polymer molecule size, and of the molecular distribution of the components employed, ensures the required bonding with the skin even at critical points of the human locomotor system, in accordance with the required function.

The high shear strength of the self-adhesive composition is achieved by the high cohesiveness of the polymer. The good finger tack is a result of the plasticizers and tackifiers employed.

The distribution of the active substances within the adhesive composition takes place in a thermal homogenizer, for example a thermal mixer, thermal kneader, roll mills or screw systems. The active substance can be added to the fully prepared adhesive composition. Alternatively, for example, the active substance can also be incorporated into an intermediate stage or into the initial mixture.

Product properties such as tack, glass transition temperature and shear stability can be quantified readily using a dynamic frequency measurement. In this case, use is made of a rheometer controlled by shearing stress. The results of this measurement method give information on the physical properties of a substance by taking into account the viscoelastic component. In this instance, at a preset constant temperature, the hot-melt pressure-sensitive adhesive is set in oscillation between two plane-parallel plates with variable frequencies and low deformation (linear viscoelastic region). Via a pickup control unit, with computer assistance, the quotient (Q=tan δ) between the loss modulus (G", viscous component) and the storage modulus (G', elastic component) is determined: Q=tan δ=G"/G'.

A high frequency is chosen for the subjective sensing of the tack, and a low frequency for the shear strength. A high numerical value denotes better tack and poorer shear stability.

The complex-dynamic glass transition point is the point of transition from the amorphous to the viscoelastic region. It corresponds to the maximum of the temperature function at a given frequency.

In accordance with the invention, preference is given to pressure-sensitive hot-melt adhesive compositions for which the ratio of the viscous component to the elastic component at a frequency of 100 rad/s at 25° C. is greater than 0.7, or to pressure-sensitive hot-melt adhesive compositions where the ratio of the viscous component to the elastic component at a frequency of 0.1 rad/s at 25° C. is less than 0.4.

The adhesive composition containing an active substance can be applied to the entire area of an appropriate conformable backing material, such as wovens, knits, films, nonwovens, paper, foam or laminates thereof, and advantageously can also be applied with areal restriction, for example by halftone printing, thermal screen printing, thermal flexographic printing or intaglio printing. This leads to particularly good air and water vapour permeability of the adhesive film.

In the case of screen printing, preference is given to application in the form of domes, especially those where the ratio of diameter to height is less than 5:1. Printed application of other forms and patterns on the backing material is also possible, for example a printed pattern in the form of alphanumeric character combinations or patterns such as matrices, stripes and zigzag lines.

In addition, the adhesive composition can also be sprayed on, for example, producing a more or less irregular applied pattern.

The self-adhesive composition can be distributed uniformly over the backing material; alternatively, it can also be applied with varying thickness or density as appropriate for the function of the product.

The principle of thermal screen printing consists in the use of a rotating, heated, seamless, drum-shaped, perforated, cylindrical screen which is fed via a nozzle with the pressure-sensitive hot-melt adhesive composition. A specially shaped nozzle lip (circular or square doctor blade) presses the self-adhesive composition, which is fed in via a channel, through the perforation of the screen wall and onto the backing web that is conveyed past it. This backing web is guided by means of a counterpressure roller against the external jacket of the heated screen drum at a rate which corresponds to the peripheral speed of the rotating screen drum.

Using this printing technique it is possible to lay down the size and shape of the domes in a defined manner. The base diameter of the domes can be chosen from 10 μm to 5,000 μm, the height of the domes from 20 μm to about 2,000 μm, preferably 50 μm to 1,000 μm, the low-diameter range being intended for smooth backings and the range of greater diameter and greater dome height being intended for rough or highly porous backing materials. The positioning of the domes on the backing is laid down in a defined manner by the geometry of the applicator unit, for example the gravure or screen geometry, which can be varied within wide limits. The backing material is preferably coated at a rate of more than 2 m/min, more preferably from 20 to 100 m/min, the chosen coating temperature being greater than the softening temperature of the adhesive system.

The pressure-sensitive hot-melt adhesive composition can be applied to the backing material with a weight per unit area of more than 15 g/m$^2$, preferably between 90 g/m$^2$ and 400 g/m$^2$ and, with very particular preference, between 130 g/m$^2$ and 300 g/m$^2$.

The percentage area that is coated with the hot-melt pressure-sensitive adhesive composition should be at least 20% and can range up to about 95%, for specific products preferably from 40 to 60% and from 70% to 95%. This can be achieved, if desired, by means of multiple application, with the possible use if desired of adhesive compositions having different properties.

Depending on the backing material and on its temperature sensitivity, the self-adhesive layer can be applied directly or first applied to an auxiliary support and then transferred to the ultimate backing. Subsequent calendering of the coated product and/or pretreatment of the backing, such as corona irradiation, may be advantageous for better anchoring of the adhesive layer.

After coating, the backing material is usually covered on the adhesive side with an anti-adhesive backing material, such as siliconized paper. The plasters are then punched out in the desired size and, if desired, are sealed individually and sterilized, preferably by means of gamma rays.

The examples which follow are intended to illustrate the invention by way of example.

EXAMPLE 1

An active substance-containing plaster, having a hot-melt self-adhesive composition which comprises a hyperaemic active substance and being suitable for use as a rheumatic plaster, was produced as follows:

A nonelastic cotton fabric having a maximum tensile strength of more than 150 N/cm and an elongation at maximum tension of less than 20%, as backing material, was coated with an adhesive composition comprising 64% by weight of A-B/A-B-A block copolymer which consists of hard and soft segments, with a ratio of A-B-A to A-B of 3:7 and with a styrene content in the polymer of 30 mol-% (Kraton G, Shell)

32% by weight of paraffinic hydrocarbon wax (H. B. Fuller)

3.5% by weight of hydrocarbon resin (Escorez, Esso)

0.3% by weight of anti-aging agent (Irganox, Ciba-Geigy) and 0.2% by weight of the hyperaemic active substance nonylic acid vanillylamide (nonivamide).

The adhesive components employed were homogenized in a thermal mixer at 175° C. for 3 h. The active substance was added in the cooling phase at 130° C., after which homogenization in the mixer was continued for 30 minutes.

The softening point of the adhesive composition was about 95° C. (DIN 52011) and the adhesive composition showed a viscosity of 2400 mPas at 150° C. (DIN 53018, Brookfield DV II, sp 21). The glass transition temperature was −10° C.

The self-adhesive composition was applied with a nozzle to the full area of the backing. Direct coating took place at 50 m/min and at a temperature of 120° C. The backing material was coated with 170 g/m$^2$.

The plaster showed good release of the active substance. After 24 hours of in vitro use on porcine skin, 15% of the active substance had been absorbed dermally. For the involatile active substance, this is a comparatively very high value. The standardized, relative proportion of the amount absorbed dermally is divided as follows:
9.2% in the horny layer
26.6% in the epidermis
64.2% in the dermis
0.0% receptor phase

EXAMPLE 2

An active substance-containing plaster with a backing material as in Example 1 was produced as follows:

The backing material was coated with an adhesive composition comprising
50% by weight of A-B/A-B-A block copolymer which consists of hard and soft segments, having a diblock content of
40% and a styrene content in the polymer of 17 mol-% (Kraton D, Shell)
44% by weight of paraffinic hydrocarbon resin (Escorez, Esso)
3.5 by weight hydrocarbon resin (Kaydol, Witco)
1.5% by weight of anti-aging agent (Irganox 1010, CibaGeigy) and
1.0% by weight of the hyperaemic active substance (nonivamide).

The adhesive components employed were homogenized in a thermal mixer at 185° C. for 2.5 h. The active substance was added in the cooling phase at 110° C., after which homogenization in the mixer was continued for 45 minutes.

The softening point of the adhesive composition was about 90° C. (DIN 52011) and the adhesive composition showed a viscosity of 1800 mPas at 175° C. (DIN 53018, Brookfield DV II, sp 21). The glass transition temperature was −5° C.

The self-adhesive composition was applied by thermal screen printing to the backing, using a 14 mesh screen from Stork with an open area of 40%. Direct coating took place at 50 m/min and at a temperature of 135° C. The amount of composition applied was 225 g/m$^2$. The air permeability of the plaster was 55 cm$^3$/cm$^2$s.

The plaster material thus produced showed a very good release rate of the active substance. After 24 hours of in vitro use on porcine skin, 17% of the active substance had been absorbed dermally. The standardized, relative proportion of the amount absorbed dermally is divided as follows:
12% in the horny layer
27% in the epidermis
61% in the dermis
0.0% receptor phase

EXAMPLE 3

An active substance-containing plaster with a backing material as in Example 1 was produced as follows using a self-adhesive composition based on a free-radically polymerized acrylate copolymer which is composed of 70% 2-ethylhexyl acrylate, 20% butyl acrylate and 10% acrylic acid. The components were reacted in solution in a reactor at 70° C. After the end point had been reached, the solvent was removed. Following concentration, the adhesive composition had a solids content of about 99%. 3% of nonivamide as active substance was incorporated into the solids in the homogenization phase. The active substance was added at 150° C., after which homogenization was continued for 90 minutes. The adhesive composition showed a viscosity of 150 Pas at 160° C. (DIN 53018, Brookfield DV II, Sp 21). The glass transition temperature was −30° C.

The self-adhesive composition was applied with a nozzle to the full area of the backing. Direct coating took place at 15 m/min and at a temperature of 165° C. The backing material was coated with 300 g/m$^2$.

The plaster material thus produced showed comparatively good release of the active substance. After 24 hours of in vitro use on porcine skin, 9% of the active substance had been absorbed dermally. The standardized, relative proportion of the amount absorbed dermally is divided as follows:
11% in the horny layer
32% in the epidermis
57% in the dermis
0.0% receptor phase

EXAMPLE 4

An active substance-containing plaster with a backing material as in Example 1 was produced as follows:

The backing material was coated with an adhesive composition comprising
64% by weight of A-B/A-B-A block copolymer which consists of hard and soft segments, having a ratio of A-B-A to A-B of 1.85 and a styrene content in the polymer of 13 mol-% (Kraton G, Shell)
26% by weight of paraffinic hydrocarbon resin (Escorez 5300, Esso Chemie)
4% by weight of paraffin oils and paraffin waxes (Shell)
0.5% by weight of anti-aging agent (Irganox 1010, CibaGeigy) and
4.0% by weight of the hyperaemic active substance capsicum extract, corresponding to 1.4% of capsaicinoids (calculated as capsaicin).

The adhesive components employed were homogenized in a thermal mixer at 175° C. for 4 h. The active substance was added in the cooling phase at 130° C., after which homogenization in the mixer was continued for 20 minutes. The degree of homogeneity achieved, relative to the target figure, was more than 90%.

The softening point of the adhesive composition was about 90° C. (DIN 52011) and the adhesive composition showed a viscosity of 2200 mPas at 175° C. (DIN 53018, Brookfield DV II, sp 21).

The self-adhesive composition was applied with a nozzle to the full area of the backing. Direct coating took place at 50 m/min and at a temperature of 120° C. The backing material was coated with 120 g/m$^2$.

The plaster material thus produced showed very good release of the active substance. After 6 hours of use, 52% of the total available amount had been released.

EXAMPLE 5

An active substance-containing plaster with a backing material as in Example 1 was produced as follows:

The backing material was coated with an adhesive composition comprising
60% by weight of A-B/A-B-A block copolymer which consists of hard and soft segments, having a ratio of A-B-A to A-B of 1.85 and a styrene content in the polymer of 13 mol-% (Kraton G, Shell)

30% by weight of paraffinic hydrocarbon resin (Escorez 5300, Esso Chemie)

7% by weight of paraffin oils and paraffin waxes (Shell/H. B. Fuller)

0.5% by weight of anti-aging agent (Irganox 1010, CibaGeigy) and 2.5% by weight of the hyperaemic active substance benzyl nicotinate.

The adhesive components employed were homogenized in a thermal mixer at 175° C. for 4 h. The active substance was added in the cooling phase at 100° C., after which homogenization in the mixer was continued for 20 minutes. The degree of homogeneity achieved, relative to the target figure, was more than 90%.

The softening point of the adhesive composition was about 92° C. (DIN 52011) and the adhesive composition showed a viscosity of 2100 mPas at 175° C. (DIN 53018, Brookfield DV II, sp 21).

The self-adhesive composition was applied to the backing by thermal screen printing, using a 14 mesh screen from Stork having an open area of 40%. Direct coating took place at 50 m/min and at a temperature of 135° C. The amount of composition applied was 225 g/m$^2$. The air permeability of the plaster was 55 cm$^3$/(cm$^2$s).

The plaster material thus produced showed very good release of the active substance. After 6 hours of use, 31% of the available amount had been released.

EXAMPLE 6

An active substance-containing plaster with a backing material as in Example 1 was produced as follows:

The backing material was coated with an adhesive composition comprising

50% by weight of A-B/A-B-A block copolymer which consists of hard and soft segments, having a ratio of A-B-A to A-B of 1.85 and a styrene content in the polymer of 13 mol-% (Kraton G, Shell)

35% by weight of paraffinic hydrocarbon resin (Escorez 5300, Esso Chemie)

7% by weight of paraffin oils (Shell)

0.5% by weight of anti-aging agent (Irganox 1010, CibaGeigy) and

10% by weight of the hyperaemic active substance propyl nicotinate.

The adhesive components employed were homogenized in a thermal kneader at 175° C. for 4 h. The active substance was added in the cooling phase at 100° C., after which homogenization in the mixer was continued for 120 minutes. The degree of homogeneity achieved, relative to the target figure, was more than 90%.

The softening point of the adhesive composition was about 82° C. (DIN 52011) and the adhesive composition showed a viscosity of 2800 mPas at 175° C. (DIN 53018, Brookfield DV II, sp 21).

The self-adhesive composition was applied to the backing by thermal screen printing, using a 14 mesh screen from Stork having an open area of 40%. Direct coating took place at 10 m/min and at a temperature of 135° C. The amount of composition applied was 200 g/m$^2$. The air permeability of the plaster was 50 cm$^3$/(cm$^2$s).

The plaster material thus produced showed very good release of the active substance and, like the plasters in the other examples, showed good adhesion properties even with the comparatively high proportion of active substance.

We claim:

1. Plasters containing active substance, comprising a hacking material and, applied thereon, a hot-melt self-adhesive composition, based on A-B or A-B-A block copolymers or mixtures thereof, where phase A is polystyrene or derivatives thereof and phase B is ethylene, propylene, butylene, butadiene, isoprene or mixtures thereof, having a proportion of diblock copolymers of less than 80% by weight, and wherein the hot-melt self-adhesive composition comprises at least one hyperaemic active substance.

2. Plasters containing active substance according to claim 1, wherein the hot-melt self-adhesive composition is based on an A-B/A-B-A block copolymer of styrene, ethylene and butylene.

3. Plasters containing active substance according to claim 2, wherein the hot-melt self-adhesive composition contains from about 0.1 to 10% by weight of nonivamide.

4. Plasters containing active substance, comprising a backing material and, applied thereon, a hot-melt self-adhesive composition, based on A-B or A-B-A block copolymers or mixtures thereof, where phase A is polystyrene or derivatives thereof and phase B is ethylene, propylene, butylene, butadiene, isoprene or mixtures thereof, the overall content of styrene in the polymer is less than 35% by weight, and wherein the hot-melt self-adhesive composition comprises at least one hyperaemic active substance.

\* \* \* \* \*

UNITED STATES PATENT AND TRADEMARK OFFICE
CERTIFICATE OF CORRECTION

PATENT NO. : 6,488,958 B1
DATED : December 3, 2002
INVENTOR(S) : Peter Himmelsbach et al.

It is certified that error appears in the above-identified patent and that said Letters Patent is hereby corrected as shown below:

<u>Title page,</u>
Item [75], Inventors, change "Rubker Strasse" to -- Buxtehude --; "Graf Anton Weg" to -- Hamburg --; "Eppendorfer Weg" to -- Hamburg --; "Feldstrasse" to -- Pinneburg --; and "Rothenhauschausee" to -- Hamburg, all of Germany --.

Signed and Sealed this

Eighteenth Day of May, 2004

JON W. DUDAS
*Acting Director of the United States Patent and Trademark Office*